United States Patent [19]

Schwan

[11] 4,128,711
[45] Dec. 5, 1978

[54] 1-[[1H-PYRROL-2-YLMETHYLENE]AMINO]-2,4-IMIDAZOLIDINEDIONE

[75] Inventor: Thomas J. Schwan, Norwich, N.Y.

[73] Assignee: Morton-Norwich Products, Inc., Norwich, N.Y.

[21] Appl. No.: 839,909

[22] Filed: Oct. 6, 1977

[51] Int. Cl.$^2$ ............................................. C07D 207/50
[52] U.S. Cl. .................................. 542/420; 424/273 R
[58] Field of Search ......................... 542/420; 548/309

[56] References Cited

U.S. PATENT DOCUMENTS

| | | | |
|---|---|---|---|
| 3,843,636 | 10/1974 | White | 542/420 |
| 3,883,516 | 5/1975 | Bailey | 542/420 |
| 4,049,650 | 9/1977 | White | 542/420 |

*Primary Examiner*—Arthur P. Demers
*Attorney, Agent, or Firm*—Anthony J. Franze

[57] ABSTRACT

A compound 1-[[1H-pyrrol-2-ylmethylene]amino]-2,4-imidazolidinedione possesses pharmacological activity as a muscle relaxant.

1 Claim, No Drawings

1-[[1H-PYRROL-2-YLMETHYLENE]AMINO]-2,4-IMIDAZOLIDINEDIONE

This invention relates to chemical compounds. In particular, it is concerned with the compound 1-[[1H-pyrrol-2-ylmethylene]amino]-2,4-imidazolidinedione.

This compound elicits pharmacological activity. In particular, it is useful as a muscle relaxant. When administered perorally to mice in doses of 50-800 mg/kg, muscle relaxant effects are produced. Such administration is readily and conveniently achieved using a carrier such as methylcellulose.

In order that this invention be readily available to and understood by those skilled in the art, the following example is supplied:

1-[[1H-Pyrrol-2-ylmethylene]amino]-2,4-imidazolidinedione

To a solution containing 14.25 g (0.15 mole) of pyrrol-2-carboxaldehyde in 100 ml 95% ethanol was added a solution of 22.80 g (0.15 mole) of 1-amino-2,4-imidazolidinedione hydrochloride in 100 ml water. A pink solid separated immediately. The mixture was diluted with 100 ml water and stirred at ambient temperature for 45 minutes. The solid was filtered, washed with 3 × 30 ml water, air dried for 1 hr., and dried at 60° for 4 hrs. to give 29.48 g (100%) of the product, m.p. 276°-279°.

Recrystallization from dimethylformamide-water gave an analytical sample, m.p. 269°-272°.

Anal. Calcd. for $C_8H_8N_4O_2$: C, 49.99; H, 4.20; N, 29.16. Found: C, 50.08; H, 4.31; N, 29.21.

What is claimed is:
1. The compound 1-[[1H-pyrrol-2-ylmethylene]amino]-2,4-imidazolidinedione.

* * * * *